United States Patent [19]

Lee et al.

[11] Patent Number: 4,793,555

[45] Date of Patent: Dec. 27, 1988

[54] CONTAINER, METHOD AND COMPOSITION FOR CONTROLLING THE RELEASE OF A VOLATILE LIQUID FROM AN AQUEOUS MIXTURE

[75] Inventors: Chi-Long Lee; Gerald A. Gornowicz, both of Midland, Mich.; Frank P. Larkin, Roswell, Ga.; Ryuzo Mikami, Ichihara, Japan

[73] Assignee: Dow Corning Corporation, Midland, Mich.

[21] Appl. No.: 184,727

[22] Filed: Apr. 22, 1988

[51] Int. Cl.[4] ............................................... A61L 9/12
[52] U.S. Cl. ........................................ 239/6; 239/53; 239/55; 239/56; 525/452; 528/28
[58] Field of Search ...................... 239/6, 34, 53-56, 239/60; 525/452; 528/28

[56] References Cited

U.S. PATENT DOCUMENTS

| | | | |
|---|---|---|---|
| 4,158,440 | 6/1979 | Sullivan et al. | 239/1 |
| 4,248,380 | 2/1981 | Lee et al. | 239/6 |
| 4,320,873 | 3/1982 | Martens, III et al. | 239/54 X |
| 4,356,969 | 11/1982 | Obermayer et al. | 239/6 |
| 4,529,124 | 7/1985 | Sullivan et al. | 239/56 |
| 4,600,146 | 7/1986 | Ohno | 239/6 |
| 4,605,165 | 8/1986 | Van Loveren et al. | 239/6 |
| 4,686,137 | 8/1987 | Ward, Jr. et al. | 428/290 |
| 4,703,070 | 10/1987 | Locko et al. | 523/102 |

FOREIGN PATENT DOCUMENTS 0218892  4/1987  European Pat. Off. .
0218891  4/1987  European Pat. Off. .

Primary Examiner—Andres Kashnikow
Assistant Examiner—Mary Beth O. Jones
Attorney, Agent, or Firm—Robert Spector

[57] ABSTRACT

Films and coatings formed from a specified class of organosiloxane/urethane copolymers are unique by virtue of their high permeability to volatile ingredients in the form of aqueous compositions and their inertness to the ingredients of these compositions. Containers wherein at least a portion of the walls comprise films or coatings formed from these copolymers are used to achieve the controlled release of volatile fragrances and biologically active agents from aqueous compositions confined within the container into the adjacent atmosphere.

8 Claims, No Drawings

CONTAINER, METHOD AND COMPOSITION FOR CONTROLLING THE RELEASE OF A VOLATILE LIQUID FROM AN AQUEOUS MIXTURE

BACKGROUND OF THE INVENTION

1. Field of the Invention

This invention relates to the controlled release of volatilized liquids. More particularly, this invention relates to a container, method and permeable materials for controlling the release of at least one volatilize ingredient, such as a fragrance or a biologically active material, from an aqueous mixture of ingredients confined within the container into the adjacent atmosphere.

2. Description of the Prior Art

Containers for volatile materials, including fragrances, air fresheners and biologically active compounds such as pheromones have been designed to control the rate at which these materials are released through at least one permeable section of the container into the atmosphere surrounding the container. The containers confine a liquid or solid composition that includes the volatile material.

Depending upon the type of volatile material and the desired release rate, the portion of the container that is permeable to the volatile material can be a layer of non-porous material such as silicon rubber, a porous film or layer of an organic polymer or a coating of an organic polymer on a porous substrate such as paper. The volatile material readily permeates through both the substrate and the coating. Containers of various configurations, both rigid and flexible, are commercially available and/or are disclosed in patents and other literature.

The exterior surface of the permeable portion of a container for dispensing a volatile material can be equipped with a temporary cover that is impermeable to the volatilized material and prevents loss of this material between the time the container is filled with the material and the time it is desired to begin releasing the material.

A variety of organic and inorganic materials have been proposed for use as the permeable portion of containers for releasing volatile materials into a gaseous environment. In accordance with the teaching of U.S. Pat. No. 4,158,440, which issued to Sullivan et al. on June 19, 1979 the volatile material is absorbed into a reservoir material that is in contact with a sheet of ultramicroporous material such as gelled cellulose triacetate into which the volatile liquid is gradually absorbed and released from the container.

The use of thin polymeric membranes having pore diameters of from $10^{-3}$ to $10^{-1}$ microns to control the release of vapors from a non-flowing liquid confined in a reservoir is taught in U.S. Pat. No. 4,356,969, which issued to Obermayer et al. on Nov. 2, 1982. The material of the membrane is one that will preferentially absorb the volatile liquid and the diameter of the pores is sufficient to allow the volatile liquid to pass through and vaporize from the pores without allowing non-vaporized liquid to arrive at the outer surface of the membrane. To release an organic liquid fragrance the membrane is preferably formed from an organophillic polymer such as cellulose triacetate, polyethylene, polypropylene or a composite of one of these polymers and a liquid.

U.S. Pat. No. 4,600,146 to Ohno, which issued on July 15, 1986 teaches confining a vaporizable liquid in a capillary tube formed from a polymeric material that is permeable to the vaporized or unvaporized liquid. The polymeric material can be an organic polymer or an organopolysiloxane.

U.S. Pat. No. 4,605,165, which issued to Van Loveran et al. on August 12, 1986 discloses containers for dispensing a volatile composition at a constant rate. The composition is allowed to permeate through a layer of porous polymer that is from 0.0025 to 0.5 mm thick. The composition of the polymer layer is defined in terms of its ability to (a) transport water vapor at a rate of between about 50 and 1000 g/m²/day at a temperature of about 25 C. and a relative humidity of about 50%, or (b) transport air at a rate of 100-20,000 Gurley seconds. The only exemplified polymer is polypropylene containing a calcium carbonate filler.

Published European Application No. 218,891, which issued on Apr. 22, 1987 discloses a container for dispensing a volatile substance into the atmosphere adjacent to the container. The container is formed from silicone rubber and the substance diffuses through the silicon rubber into the environment surrounding the container. The high permeability of silicone rubber to gasses is allegedly responsible for the high rates of release that can be achieved. The application does not contain examples or data disclosing the rate at which any specific material is released.

Published European Application No. 218,892, which issued on Apr. 22, 1987, describes a dispenser for releasing a volatile liquid. The container comprises an open-ended hollow body formed from a material that is impermeable to the volatile liquid and a closure for the container that is in contact with the volatile liquid. The closure is formed from a silicone rubber and is permeable to the volatile liquid. No experimental data regarding release rates are provided.

For some end use applications it is advantageous to incorporate a volatile fragrance, air freshener or biologically active compound such as a bactericide, herbicide or the sex pheromone of an insect pest into an aqueous mixture from which the liquid is subsequently volatilized and released into the atmosphere. In this instance the release rate of the volatile liquid is proportional to its partial pressure in the mixture and the permeability of the material separating the aqueous mixture from the atmosphere.

Controlled release into the atmosphere of volatile liquids from an aqueous mixture has been achieved by confining the mixture in a container wherein the composition is in contact with the inner surface of a layer of a porous foam formed from organic polymer. The outer surface of the foam is exposed to the environment into which the volatilized liquid is to be released.

The disadvantage of such an container is that if the foam is sufficiently porous to achieve the desired release rate of the volatile material, which can be from 0.1 to 100 mg/(cm²×day), depending upon the nature of the material being released, the foam layer also permits the other less volatile ingredients of the aqueous mixture, to permeate the foam layer at a rate exceeding their evaporation rate, thereby allowing these ingredients to accumulate on the exposed surface of the foam layer.

One solution to this problem is to locate the porous foam layer out of direct contact with a reservoir containing the aqueous mixture. The mixture is allowed to diffuse to the foam layer through a wick of absorbent material. A disadvantage of such an arrangement is that the exposed surface of the foam can be wet if the rate at which the aqueous composition permeates through the foam is greater than the evaporation rate of the less volatile ingredients, particularly water. A more serious disadvantage is that when the container is placed in a position that allows the aqueous mixture to flow out of the reservoir and contact the foam layer, the mixture typically leaks through the foam and out of the container.

The problems of liquid accumulation and leakage can be avoided by covering or replacing the porous foam layer with a film or coating of a material that is impervious to the aqueous mixture while allowing vaporized liquids from the mixture to penetrate and be released into the atmosphere adjacent to the film or coating. For many volatile materials it is desirable that the rate at which the liquids are released through the film or coating be at least about 70 percent of the release rate through the uncovered porous polymer layer and that the exposed surface of the film or coating remain dry during the entire release period. The present inventors endeavored to find materials that satisfy these two criteria.

Membranes of silicone rubber such as those disclosed in the aforementioned published European Patent Applications were insufficiently permeable to provide the desired rapid release rate of a volatilized fragrance from an aqueous mixtures Films and coatings formed from the hydrophobic organic polymers disclosed in the aforementioned U.S. Pat. No. 4,605,165 to Van Loveran et al. were unsuitable for the same reason.

Films and coatings formed from hydrophilic polymers such as polyoxyethylene glycols release the volatile ingredients of aqueous mixtures considerably more rapidly than silicone rubber or hydrophobic organic polymers. The present inventors found these hydrophilic polymers to have the same disadvantage, namely leakage of the aqueous mixture, as the porous hydrophobic polymers they were intended to coat or replace, resulting in accumulation of liquid on the exposed surface of the film or coating. In addition these hydrophilic polymers are susceptible to solubilization and/or excessive swelling by the aqueous mixture, resulting in frequent rupturing of the film or coating.

U.S. Pat. No. 4,686,137, which issued to Ward and Riffle on Aug. 11, 1987, discloses moisture vapor permeable block copolymers consisting essentially of a "hard" segment that is preferably a polyurethane formed from the reaction of diphenylmethane diisocyanate with a diol. and a "soft" segment having both hydrophilic and hydrophobic portions. The hydrophobic portion of the soft segment can be a polymeric tetraalkylene oxide, such as polytetramethylene oxide, a polydialkylsiloxane, or a mixture of these two polymers, and the preferred hydrophilic segment is polyethylene oxide. These copolymers are combined with a base polymer, such as a polyurethane, and a suitable solvent to form films suitable for use as wound dressings or semipermeable membranes and as coating compositions for textile materials.

An objective of this invention is to provide materials for films or coatings that are inert to aqueous mixtures while allowing volatile ingredients of these mixtures to migrate through the film or coating and be released into an adjacent gaseous environment at a suitably rapid rate without the accumulation of liquid material on the exposed surface of the film or coating. These films or coatings can be used alone or in combination with a layer of porous organic or inorganic material to control the release rate of the volatile ingredients.

SUMMARY OF THE INVENTION

The present inventors discovered that films and coatings formed from certain segmented block copolymers that are outside the scope of those described in the aforementioned U.S. Pat. No. 4,686,137 are unique by virtue of (1) their high permeability to the volatile liquid ingredients of aqueous mixtures, (2) their ability to limit the transport of water vapor to a rate that will maintain the surface exposed to the atmosphere dry to the touch, and (3) their resistance to excessive swelling and/or degradation by other ingredients of the mixtures, particularly water.

The present copolymers comprise a hard segment derived from the reaction of an organic diisocyanate with a diol and a soft segment containing at least one sequence of dimethylsiloxane units as a hydrophobic portion and at least one sequence of oxyethylene units as a hydrophylic portion. Films and coatings formed from these copolymers are particularly useful for controlling the release of fragrances and other volatile liquid ingredients from confined aqueous mixtures into the atmosphere.

DETAILED DESCRIPTION OF THE INVENTION

This invention provides an improved container for controlling the release into the adjacent atmosphere of at least one volatile liquid ingredient from an aqueous mixture confined in said container, where (a) at least one wall of said container comprises at least one release-controlling layer of a material that is inert with respect to said mixture and permeable to said volatile ingredient, (2) said layer comprises an inner surface in contact with said mixture and an outer surface in contact with said atmosphere, and where the improvement comprises the presence of said layer as a 0.001 to 1 mm.—thick film or coating of a substantially linear dimethylsiloxane/oxyethylene/urethane block copolymer comprising from 20 to 40 weight percent of hard segments consisting essentially of polyurethane units derived from an organic diisocyanate and an alkylene diol, and from 60 to 80 weight percent of soft segments comprising from 15 to 65 percent by weight, based on the weight of said copolymer, of a hydrophobic portion consisting essentially of at least one sequence of from 15 to about 100 dimethylsiloxane units and from 10 to 65 percent by weight, based on the weight of said copolymer, of a hydrophylic portion consisting essentially of at least one sequence of from 5 to 70 oxyethylene units, where the molar ratio of hard to soft segments is from 2.5 to 7.

This invention also provides an improved method for achieving release of at least one volatile liquid ingredient of an aqueous mixture from a container into the adjacent atmosphere, at a controlled rate by separating said mixture from said atmosphere by means of a release-controlling layer of a polymeric material that is from 0.001 to 1 mm. thick and permeable to said ingredient, where the improvement resides in selecting said polymeric material from the substantially linear block copolymers described in the preceding paragraph.

Another aspect of this invention relates to compositions for preparing a film or coating that allows at least one volatile liquid ingredient of an aqueous mixture in contact with one surface of said coating or film to permeate at a rate of from 0.1 to 200 mg./cm.$^2$/24 hours at a temperature of 20° C. into a gaseous atmosphere in contact with the opposite surface of said coating or film. The composition comprises at least one of the substantially linear dimethylsiloxane/oxyethylene/urethane block copolymers of this invention. Depending upon the method used to fabricate the polymer, the composition can optionally contain a solvent for the copolymer. If the composition will be used to apply a coating of the copolymer, the solvent should have a boiling point of from about 60 to about 120° C. in order to minimize the amount of heating required to remove the solvent and form the film or coating.

The rate-controlling layer through which the volatile ingredients of the aqueous mixture are released from the container into the adjacent atmosphere comprises a dimethylsiloxane/polyoxyethylene/urethane copolymer. This layer can be a self-supporting film or an adherent coating on a variety of porous substrates, including cellular organic polymers such as polyethylene, fibrous materials such as paper and porous inorganic material such as sintered glass or metal.

The present block copolymers contain at least one segment of a "hard" polymer and at least one segment of a "soft" polymer. It is understood in the art that the terms "hard" and "soft" as applied to segments of block copolymers refer to the relative durometer hardness values exhibited by these segments when evaluated as homopolymers.

The hard segment of the present copolymers is a polyurethane derived from an organic diisocyanate and a low molecular weight diol, sometimes referred to as a chain extender. Any of the available aliphatic, aromatic or cycloaliphatic diisocyanates can be used to prepare the polyurethane portion of these copolymers. Preferred diisocyanates include but are not limited to p-tolylene diisocyanate, 4,4'-diphenylmethanediiosocyanate and 4,4'-dicyclohexylmethanediisocyanate.

The diol portion of the polyurethane can be any of the available aliphatic diols containing from 2 up to about 10 carbon atoms. Diols containing from 2 to 4 carbon atoms are preferred, based on the availability of these compounds.

The hard segment constitutes from 20 to 40 weight percent of the copolymer, preferably from 25 to 35 weight percent, and the molar ratio of hard segment (diisocyanate and aliphatic diol units) to soft segments (polydimethylsiloxane and polyoxethylene units) is from 2.5 to 7, preferably about 5.

The soft segment of the present copolymers includes a hydrophylic and a hydrophobic portion. The hydrophobic portion of the copolymer molecules consists essentially of at least one sequence of from 15 to about 100 dimethylsiloxane units, and these sequences constitute from 15 to 65 weight percent of the copolymer. These sequences preferably contain from 20 to 40 dimethylsiloxane units and constitute from 40 to 65 weight percent of the copolymer. Methods for preparing functionally substituted polydimethylsiloxanes and copolymerizing these polymers with diisocyanates and other organic monomers are known in the art and do not form part of this invention.

The hydrophylic portion of the soft segment consists essentially of at least one sequence per copolymer molecule of from 5 to 70 oxyethylene units, which can be present as part of the linear portion of the copolymer or as pendant groups attached to the diorganosiloxane units. The oxyethylene units constitute from 10 to 65, preferably from 15 to 30, weight percent of the copolymer.

The optimum molecular weight range for a given copolymer will be determined by the desired physical properties of the copolymer, such as tensile strength, elongation and tear strength, and the method used to fabricate the rate-controlling layer. If the copolymer is to be shaped into a self-supporting film as the rate controlling layer, the weight average molecular weight of the copolymer is preferably from 50,000 to about 500,000. If the rate-controlling layer is prepared by coating a copolymer of this invention on a porous substrate, the weight average molecular weight of the copolymer is typically in the range of from 25,000 to about 300,000 to facilitate solubilization of the copolymer in the solvent used to prepare the coating composition.

Methods for preparing dimethylsiloxane/urethane/oxyethylene copolymers are described in patents and other literature, including the aforementioned U.S. Pat. No. 4,686,137 to Ward and Riffle. In accordance with a preferred method a liquid polydimethylsiloxane containing from about 15 to about 100 repeating units per molecule and a monofunctional isocyanate-reactive group such as

at the two terminal positions is reacted with the organic diisocyanate and a polyethylene glycol or polyethylene oxide by heating the mixture in the presence of a suitable catalyst. The aliphatic glycol that forms part of the hard segment is then added to the reaction mixture and heating is continued until substantially all of the isocyanate reacts, which typically requires from 2 to 16 hours. The reaction is preferably conducted under an inert atmosphere such as nitrogen using as the reaction medium at lest one organic liquid such as toluene, tetrahydrofuran and N,N-dimethylformamide that will dissolve all of the reactants and the resultant copolymer.

The substituents represented by R and R" in the preceding formula are monovalent hydrocarbon radicals and R' represents an alkylene radical.

Films or coatings of the present copolymers control the rate at which the volatile ingredients of aqueous compositions are released from a container comprised at least in part of the film or coating into the atmosphere adjacent to the container. Depending upon the release rate of the copolymer and the rate at which it is desired to release the volatile material(s), the present films and coatings constitute from less than 1 percent of the surface area of the container up to the entire surface area that is exposed to the adjacent atmosphere. In some instances the entire container can be fabricated from one of the present copolymers.

The present block copolymers are thermoplastic and can be processed to form coatings and films using any of the known techniques for fabricating thermoplastic organic polymers. These techniques include but are not limited to pressing, calendering, and extrusion of bulk copolymers and dissolving the copolymers to form solutions that are then applied to a suitable substrate to form coatings as thin as 0.001 mm.

One embodiment of the present containers are rigid or semi-rigid and can be fabricated into a variety of shapes. Alternatively, the container can be in the form of a flexible pouch that is suitable sealed to prevent leakage of the aqueous composition. The shape, flexibility and size of the containers are not critical to their performance in accordance with the present method, and are typically determined by aesthetic considerations and the end use application of the container.

Containers that are impervious to the ingredients of the present aqueous compositions of this invention can be formed from naturally occurring materials such as wood, ceramic materials such as porcelain, non-porous synthetic organic polymers such as polyethylene, polystyrene, polyesters, epoxy resins, phenolic resins and organic or silicone elastomers. These containers have at least one gap or aperture that is completely covered by one of the present copolymers in the form of a self-supporting film or a coating on a porous substrate. The volatile ingredients of an aqueous composition confined in the container migrate through this film or coating into the atmosphere surrounding the container.

The apertures or open areas in otherwise impermeable containers that are covered by coatings or films of the present copolymers to form release-controlling layers range from 1 cm. up to 10 cm. or more in diameter, depending upon the desired release rate and the design of the container, and the coating or film can be from 0.001 up to 1 mm. in thickness.

Alternatively one of the present copolymers constitutes the entire exterior surface of the container. The copolymer can be in the form of a self-supporting film or a coating on a self-supporting porous support such as a porous organic polymer. Methods for forming such containers are known in the art, and do not form part of this invention.

As discussed previously in this specification virtually any volatile material that is compatible with water and will not excessively swell or dissolve the present copolymers can be released into the atmosphere using a container of this invention. Such materials include but are not limited to fragrances, perfumes, air fresheners and deodorizers, biologically active compounds such as disinfectants, bactericides, insecticides, attractants and repellents for both insects and animals, sex pheromones of insect pests such as the mosquito and fruit fly, plant nutrients, fertilizers, herbicides and plant growth regulators.

The following examples describe preferred embodiments of the present containers, copolymers and volatile materials. The examples should not be interpreted as restricting the scope of the invention as defined in the accompanying claims. Unless otherwise specified, all parts and percentages in the examples are by weight and viscosity values were measured at 25° C.

EXAMPLE 1

Two dimethylsiloxane/urethane/oxyethylene block copolymers of this invention and three control copolymers were prepared by placing the amounts specified in the following Table I of 4,4'-dicyclohexylmethane diisocyanate (HMDI) and from 100 to 500 cc of toluene in a glass reactor equipped with a stirring blade, reflux condenser, addition funnel and filled with a nitrogen atmosphere. A toluene solution of a polydimethylsiloxane (PDMS) containing an average of about 30 dimethylsiloxane units per molecule and terminal units of the formula

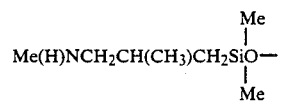

was then added over a period of 30 minutes to the reaction mixtures for polymers 1, 2, A, B and C, at which time a toluene solution of a polyethylene oxide (PEO) having a molecular weight of 1540 was added to the reaction mixtures for polymers 1, 2, B and C. 0.3 cc. of a 10 percent by weight solution in toluene of dibutyltin dilaurate was added to all of the reaction mixtures as the polymerization catalyst, and the resultant mixtures were heated at a temperature of 100° C. for one hour. The amount of 1,4-butanediol (BD) specified in the following Table I was then added and the reaction mixtures were heated at a temperature of 95° C. for about 16 hours.

Each of the polymers was isolated by pouring the reaction mixture into a shallow dish and allowing it to cool. The resultant swollen polymer was cut into small pieces and the solvent removed by evaporation. The tensile strength, elongation and weight average molecule weight of the polymers are reported in Table II. Films were formed by compression molding of the polymers at 20,000 psi and a temperature of 165° C. for 5 minutes using sheets of Teflon(R) as release layers.

The amounts of the four reactants together with the weight percentages of polydimethylsiloxane and polyethylene oxide are listed in Table I. The polymers identified as A, B, and C are outside the scope of the present invention, and were prepared for comparative purposes.

TABLE I

| | Polymer Compositions | | | |
|---|---|---|---|---|
| Polymer | HMDI (g.) | BD (g.) | PDMS (g./%) | PEO (g./%) |
| 1 | 106.0 | 23.85 | 156.20/40 | 105.5/27 |
| 2 | 106.0 | 23.85 | 218.20/53 | 63.80/15 |
| A | 318.0 | 71.60 | 921.00/70 | 0.00/0 |
| B | 133.3 | 30.15 | 25.96/6 | 236.98/56 |
| C | 100.00 | 22.9 | 0.00/0 | 234.20/66 |

TABLE II

| | Physical Properties | | |
|---|---|---|---|
| Polymer | Tensile Strength psi (Mpa) | Elongation (%) | Mw |
| 1 | 2,535 (17.5) | 940 | 178,000 |
| 2 | 1,420 (9.7) | 600 | 230,000 |
| A | 2,125 (14.7) | 335 | 136,000 |
| B | 800 (5.5) | 170 | 54,300 |
| C | 700 (4.9) | 265 | 50,700 |

EXAMPLE 2

This example demonstrates the ability of the present copolymers to provide a high rate of release of benzyl alcohol from an aqueous solution confined in a container covered with a film of the copolymer into the atmosphere surrounding the container.

Fisher/Payne permeability cups were used to determine the rate at which benzyl alcohol was released from a 3% by weight solution of this compound in water. About 10 cc of this solution were placed in the cup, after which a disk cut from a film of the copolymer to be evaluated was placed over the cup flange and secured in position by means of clamps under sufficient pressure to ensure a tight seal when the cup was inverted.

The transmission rates through the films were determined using a procedure similar to the one described in test method E-96-80, published by the American Society for Testing and Materials. The cups containing the benzyl alcohol solutions were inverted, allowing the solution to completely cover the copolymer films and the cups were maintained at a temperature of 20° C. and a relative humidity of 50% for one week. The cups were weight at 24 hours intervals to determine the amount of material that had volatilized through the polymer films. These values were used to calculate the volatilization rate (VR) for the composition expressed as $(g \times mm)/(cm^2 \times 24\ hours)$, where $(g \times mm)/cm^2$ represents the weight loss that would be measured during a given 24 hour period for a 1 mm.-thick film having a surface area of 1 square centimeter.

The polymers used were polymers 1, 2, A, B, and C described in Table I of Example 1. The thickness of the actual films were 0.457 mm. for polymers 1 and 2, 0.5 mm. for polymer A, 0.25 mm. for polymer B and 0.3 mm for polymer C. The volatilization rate for the 4 samples tested are listed in Table III. Polymers B and C ruptured during the testing period sometime prior to the second day, and are therefore not included in Table III.

TABLE III

| Volatilization Rate $(g. \times mm)/(cm^2 \times 24\ Hours)$ For Aqueous Benzyl Alcohol | | | |
|---|---|---|---|
| Day | Polymer 1 | Polymer 2 | Polymer A |
| 1 | 0.02396 | 0.01294 | 0.0117 |
| 2 | 0.02486 | 0.01384 | 0.00913 |
| 3 | 0.02562 | 0.01414 | 0.00689 |
| 6 | 0.02589 | 0.01456 | 0.00497 |
| 8 | — | 0.01444 | 0.00428 |
| 10 | — | 0.01390 | 0.00383 |
| 12 | — | 0.01350 | 0.00360 |
| 13 | — | 0.01325 | 0.00346 |

These data demonstrate that films formed from the copolymers of this invention not only released benzyl alcohol from an aqueous solution at a faster rate than polymer A, but also maintain this rate of release throughout the test period whereas the release rate through polymer A gradually decreases.

EXAMPLE 3

This example demonstrates the ability of a film formed from polymers 1 and 2 of Example 1, two copolymers of this invention, to release a volatile pheromone at an effective rate from an aqueous solution, and the inability of a control copolymer, Polymer A of Example 1, to function properly in this application.

The evaluation procedure and conditions described in the preceding Example 2 were employed using a 0.002 percent solution of "Trimedlure", a commercially available pheromone of the Mediterranean fruit fly, in a 95/5 weight ratio mixture of water/ethanol. The release rates obtained are reported in the following Table IV. The thickness of the films formed from polymers 1, 2 and A were 0.425 mm., 0.475 mm. and 0.45 mm.

TABLE IV

| Volatilization Rate of Trimedlure Solution $(g. \times mm)/(cm^2 \times 24\ Hours)$ | | | |
|---|---|---|---|
| Day | Polymer 1 | Polymer 2 | Polymer A |
| 1 | 0.0208 | 0.00534 | 0.02156 |
| 2 | 0.0247 | 0.00828 | 0.02645 |
| 3 | 0.0253 | 0.00810 | 0.01965 |
| 4 | 0.0253 | 0.00784 | 0.01507 |
| 7 | 0.0258 | 0.00846 | 0.00945 |

The data in Table IV demonstrate that the rate at which a given volatile material is released from an aqueous composition can be controlled by varying the composition of the copolymer. It will also be noted that while the rate of release through the control copolymer A decreased during the evaluation period, the rates of release through the two copolymers (1 and 2) of this invention increased during the same period.

EXAMPLE 4

This example compares the abilities of two polymers of this invention (polymers 1 and 2 of Example 1), a control copolymer without oxyethylene units (polymer A of Example 1) and a commercially available polydimethylsiloxane elastomer composition (identified as polymer D) to control the release of an aqueous mixture containing an air freshener as the volatile material.

Portions weighing about ten grams each of an aqueous fragrance composition obtained from a commercial wick-type air freshener dispenser were placed in Fisher-Payne cups that were then covered with films formed from polymers 1, 2, and A described in the foregoing Example 1 and from a peroxide-cured polydimethylsiloxane elastomer composition (polymer D) available as WC-50 from the Dow Corning Corporation of Midland, Mich. The films were molded under the conditions described in Example 2.

After being sealed with the films the cups were inverted. The cups were weighed daily over a nine day period, with the exception of Saturday and Sunday, and the permeability $(mg \times mm)/(cm^2 \times 24\ hours)$ of the aqueous fragrance mixture was calculated using these weight loss values. The films formed from polymers 1 and 2 were 0.4 mm thick, the film formed from Polymer A was 0.2 mm thick and the film formed from the polydimethylsiloxane elastomer composition (polymer D) was 0.5 mm thick.

The results of the permeability determinations are recorded in Table V.

TABLE V

| Permeability of Aqueous Fragrance Composition | | | | |
|---|---|---|---|---|
| Permeability $(mg \times mm)/(cm^2 \times 24\ hours)$ | | | | |
| Day | Polymer 1 | Polymer 2 | Polymer A | Polymer D |
| 1 | 34.64 | 19.55 | 10.80 | 17.50 |
| 2 | 38.04 | 21.68 | 9.30 | 17.31 |
| 3 | 36.13 | 20.83 | 7.90 | 12.63 |
| 4 | 34.21 | 20.40 | 7.30 | 21.00 |
| 7 | 32.23 | 17.85 | 5.47 | 9.33 |
| 8 | 28.90 | 14.66 | 4.20 | 8.50 |
| 9 | 26.78 | 14.45 | 3.80 | 6.67 |

These data demonstrate the higher permeability of the present copolymers to an aqueous fragrance mixture relative to the permeability of either a copolymer without oxyethylene units (polymer A) or a polydimethylsiloxane elastomer (polymer D) of the type disclosed in the prior art as suitable for the release of a pure fragrance into the atmosphere.

EXAMPLE 5

This example demonstrates the ability of a coating formed from one of the present copolymers to release a fragrance from an aqueous mixture at a useful rate without allowing the less volatile ingredients of the mixture to collect on the exposed surface of the coating. A commercially available wick type air freshener dispenser was used to release the fragrance through a disk of polyethylene foam. The exposed surface of the disks on two dispensers were coated with a 10 percent solution of polymer 2 described in the preceding example 1 in a solvent formed by mixing equal parts by weight of toluene, methylethyl ketone and tetrahydrofuran. The coating was applied using a paint sprayer and allowed to dry for one day. The concentration of polymer on the surface of the foam was 7.5 mg/cm$^2$. An air freshener dispenser with an uncoated foam disk as the release-controlling layer was used as the control.

The amount of fragrance released through the two coated foam disks and the uncoated control disk was determined by weighing each of the dispensers daily over a 30 day period, with the exception of Saturdays and Sundays. The weight lost by the three dispensers during this period is recorded in Table VI in addition to the weight loss of the dispensers with the coated foam disks relative to weight loss of the control dispenser, expressed as a percentage, (W/w)×100, where W represents the weight loss through the coated foam for the specified one-day period and w represents the weight loss through the uncoated control foam during the same period.

The exposed surface of each foam layer was also examined daily both visually and by touching it to determine whether any liquid was present. The two coated foams remained dry to the touch throughout the test period, whereas the uncoated control was wet at day 1 and remained wet throughout the test period.

TABLE VI

Weight of Fragrance Released Through Coated and Uncoated Foam Disks

| | Weight Loss (grams) | | |
|---|---|---|---|
| Day | Coated Foam (No. 1/No. 2) | Uncoated Control Foam | W/w × 100 (No. 1/No. 2) |
| 1 | 6.53/6.33 | 6.33 | 94/91 |
| 2 | 12.05/11.65 | 12.03 | 97/94 |
| 5 | 26.20/25.03 | 26.54 | 99/94 |
| 6 | 30.23/28.83 | 30.56 | 99/94 |
| 7 | 33.75/32.24 | 34.14 | 99/94 |
| 8 | 36.76/35.25 | 37.20 | 99/95 |
| 9 | 39.84/38.29 | 40.35 | 99/95 |
| 12 | 47.66/46.15 | 48.28 | 99/96 |
| 13 | 50.08/48.56 | 50.75 | 99/96 |
| 14 | 52.24/50.71 | 52.97 | 99/96 |
| 15 | 54.30/52.75 | 55.11 | 99/96 |
| 16 | 56.32/54.73 | 57.20 | 98/96 |
| 19 | 61.84/59.97 | 62.75 | 99/96 |
| 20 | 63.51/61.49 | 64.43 | 99/95 |
| 21 | 65.15/62.97 | 66.06 | 99/95 |
| 23 | 68.02/65.68 | 68.95 | 99/95 |
| 26 | 72.08/69.61 | 73.01 | 99/95 |
| 28 | 74.53/72.00 | 75.42 | 99/95 |
| 29 | 75.73/73.16 | 76.57 | 99/96 |
| 30 | 76.95/74.28 | 77.69 | 99/96 |

These data demonstrate the ability of the coatings formed from the present copolymers to maintain a dry release surface without substantially decreasing the rate at which a volatile fragrance is released in the absence of the coating.

EXAMPLE 6

This example demonstrates the ability of the present copolymers to be pigmented without adversely affecting the permeability of films and coatings formed from these copolymers to the volatile ingredients of aqueous mixtures.

Twelve parts of No. 18 blue pigment was blended with 200 parts of a 13 percent solution of polymer 2, described in the foregoing Example 1, by processing the mixture in a ball mill for about 16 hours. The solvent was a mixture of 1 part tetrahydrofuran, 1 part toluene and 2 parts methylethyl ketone. The resultant solution was used to coat a 3 mm-thick disk of polyethylene foam by spraying the foam with the pigmented solution to achieve a coating weight of about 0.0024 g/cm$^2$.

The coated disk replaced the uncoated disk of a commercial wick type air freshener dispenser. The permeation rate of the fragrance through the coated disk was compared with the rate of the same fragrance through an uncoated control disk over a two day period as described in the preceding Example 5. At the end of one day the permeation rate through the coated disk was 98.6 percent of the rate exhibited by the control. After the second day this value had increased to 99.3 percent. At the end of the evaluation period both of the coated foams were dry to the touch, whereas the uncoated control was damp.

That which is claimed is:

1. In a container for controlling the release from said container into the adjacent atmosphere of at least one volatile liquid ingredient of an aqueous mixture, where
   (1) at least one wall of said container comprises at least one release-controlling layer of a solid material that is inert with respect to said mixture and permeable to said ingredient, and
   (2) said layer comprises an inner surface in contact with said mixture and an outer surface in contact with said atmosphere,
the improvement comprising the presence of said layer as a 0.001 to 1 mm.-thick film or coating of a substantially linear dimethylsiloxane/oxyethylene/urethane copolymer comprising from 20 to 40 weight percent of hard segments consisting essentially of polyurethane units derived from an organic diisocyanate and an alkylene diol, and form 60 to 80 weight percent of soft segments comprising from 15 to 65 percent by weight, based on the weight of said copolymer, of a hydrophobic portion consisting essentially of at least one sequence of from 15 to about 100 dimethylsiloxane units and from 10 to 65 percent by weight, based on the weight of said copolymer, of a hydrophylic portion consisting essentially of at least one sequence of from 5 to 70 oxyethylene units, where the molar ratio of hard to soft segments is from 2.5 to 7.

2. A container according to claim 1 where said atmosphere is air; said ingredient is selected from a fragrance, an air freshener, an air deodorizer, an insert repellant and an insect sex pheromone; the hard segment of the copolymer constitutes from 25 to 35 percent by weight of the copolymer; the organic diisocyanate is an aromatic or cycloaliphatic diisocyanate; the alkylene diol contains from 2 to 10 carbon atoms; the dimethylsiloxane sequences contain from 20 to 40 repeating units and constitute from 40 to 65 weight percent of said copolymer; the oxyethylene sequences constitute from 15 to 30 percent by weight of said copolymer; and the layer is a self-supporting film having a thickness of from 0.1 to 1 mm. or a coating on a porous substrate.

3. A container according to claim 2 where the organic diisocyanate selected form the group consisting of is p-tolylene diisocyanate, 4,4'-diphenylmethane diisocyanate and 4,4'-dicyclohexylmethane diisocyanate; the alkylene diol is 1,4-butanediol; and the molar ratio of hard to soft segments is about 5.

4. A container according to claim 1 where the walls of said container are rigid, are formed from a material that is impervious to said ingredient and contain at least one aperture that is covered with said release-controlling layer in the form of a self-supporting film of said copolymer or a coating of said copolymer on a porous support.

5. A container according to claim 4 where said porous support is a foamed organic polymer.

6. In a method for achieving release of at least one volatile liquid ingredient of an aqueous mixture into a gaseous atmosphere at a controlled rate by separating said mixture from said atmosphere by means of a release controlling layer of a solid material that is inert with respect to said mixture, from 0.001 to 1 mm. thick and permeable to said ingredient, where the improvement is characterized by selecting the material of said release controlling layer from substantially linear dimethylsiloxane/oxyethylene/urethane block copolymers comprising from 20 to 40 weight percent of hard segments consisting essentially of polyurethane units derived from an organic diisocyanate and an alkylene diol, and from 60 to 80 weight percent of soft segments comprising from 15 to 65 percent by weight, based on the weight of said copolymer, of a hydrophobic portion consisting essentially of at least one sequence of from 15 to about 100 dimethylsiloxane units and from 10 to 65 percent by weight, based on the weight of said copolymer, of a hydrophylic portion consisting essentially of at least one sequence of from 5 to 70 oxyethylene units, where the molar ratio of hard to soft segments is from 2.5 to 7.

7. A method according to claim 6 where said atmosphere is air, said ingredient is selected form the group consisting of a fragrance, an air freshener, an air deodorizer, an insert repellant and an insect sex pheromone; the hard segment of the copolymer constitutes from 25 to 35 percent by weight of the copolymer; the organic diisocyanate is an aromatic or cycloaliphatic diisocyanate; the alkylene diol contains from 2 to 10 carbon atoms; the dimethylsiloxane sequences contain from 20 to 40 repeating units and constitute from 40 to 65 weight percent of said copolymer; the oxyethylene sequences constitute from 15 to 30 percent by weight of said copolymer; and said layer is a self-supporting film having a thickness of from 0.1 to 1 mm. or a coating on porous substrate.

8. A method according to claim 7 where the organic diisocyanate is selected from the group consisting of p-tolylene diisocyanate, 4,4'-diphenylmethane diisocyanate and 4,4-dicyclohexylmethane diisocyanate; the alkylene diol is 1,4-butanediol; and the molar ratio of hard to soft segments is about 5.

* * * * *